(12) United States Patent
Mooney

(10) Patent No.: US 12,570,962 B2
(45) Date of Patent: Mar. 10, 2026

(54) PREPARATION OF HUMAN PLATELET LYSATE (HPL) FROM REFRIGERATED WHOLE BLOOD PLATELETS

(71) Applicant: Oklahoma Blood Institute, Oklahoma City, OK (US)

(72) Inventor: Charles Mooney, Oklahoma City, OK (US)

(73) Assignee: OKLAHOMA BLOOD INSTITUTE, Oklahoma City, OK (US)

( * ) Notice: Subject to any disclaimer, the term of this patent is extended or adjusted under 35 U.S.C. 154(b) by 1060 days.

(21) Appl. No.: 17/151,458

(22) Filed: Jan. 18, 2021

(65) Prior Publication Data

US 2021/0236556 A1      Aug. 5, 2021

Related U.S. Application Data

(60) Provisional application No. 62/969,462, filed on Feb. 3, 2020.

(51) Int. Cl.
| | |
|---|---|
| *A61K 35/19* | (2015.01) |
| *C12N 5/00* | (2006.01) |
| *C12N 5/078* | (2010.01) |

(52) U.S. Cl.
CPC ......... *C12N 5/0644* (2013.01); *C12N 5/0018* (2013.01); *C12N 5/0087* (2013.01)

(58) Field of Classification Search
CPC ..... C12N 5/0018; C12N 5/0644; A61K 35/19
See application file for complete search history.

(56) References Cited

FOREIGN PATENT DOCUMENTS

| | | | | |
|---|---|---|---|---|
| WO | WO-2018091713 A1 * | 5/2018 | ............. | A61K 35/19 |
| WO | WO-2019063683 A1 * | 4/2019 | ............. | A61K 35/19 |

OTHER PUBLICATIONS

Katharina Düregger et al. "Influence of storage conditions on the release of growth factors in platelet-rich blood derivatives" Current Directions in Biomedical Engineering 2016; 2(1): 311-314 (Year: 2016).*

Mallikarjun Handigund et al. "Review: Insights into Platelet Storage and the Need for Multiple Approaches" Annals of Clinical & Laboratory Science, vol. 45, No. 6, 2015, 7pages (Year: 2015).*

Daniel Tzu-Bi Shih et al. "Preparation, quality criteria, and properties of human blood platelet lysate supplements for ex vivo stem cell expansion" New Biotechnology vol. 32, No. Jan. 1, 2015, 13 pages (Year: 2015).*

Cober et al. "Effects of different concentrations of anticoagulant on the in vitro characteristics of autologous whole blood" TRANSFUSION vol. 41, Dec. 2001, pp. 1606-1609 (Year: 2001).*

Brecher et al. "Bacterial Contamination of Blood Components" Clinical Microbiology Reviews, Jan. 2005, p. 195-204 (Year: 2005).*

Gulliksson et al. "Storage of whole blood overnight in different blood bags preceding preparation of blood components: in vitro effects on red blood cells" Blood Transfus 2009; 7: 210-215 (Year: 2009).*

CFR "Additional Standards for Human Blood and Blood Products" 21 CFR Part 640 Subpart A, Whole Blood. Nov. 20, 1973 with uptates until 2015 (Year: 2015).*

* cited by examiner

*Primary Examiner* — Thane Underdahl
(74) *Attorney, Agent, or Firm* — Barnes & Thornburg LLP

(57) ABSTRACT

Methods provided for producing human platelet lysates (HPL) typically from expired platelet units that were initially manufactured to be infused into patients. Whole blood units from which platelets will be prepared for transfusion are maintained at a temperature cooling toward room temperature. The platelet lysate produced by the method can be formed from platelets that have been removed from the refrigerated whole blood unit more than 8 hours after phlebotomy.

8 Claims, 2 Drawing Sheets

PREPARATION OF HUMAN PLATELET LYSATE (HPL) FROM REFRIGERATED WHOLE BLOOD PLATELETS

CROSS REFERENCE TO RELATED APPLICATION

This application claims the benefit of U.S. Provisional Patent Application No. 62/969,462 filed on Feb. 3, 2020, which is hereby incorporated by reference.

FIELD

This disclosure is related to blood platelet lysate obtained from refrigerated whole blood, and more specifically, the production of human platelet lysate (HPL) from platelets obtained from refrigerated whole blood units.

BACKGROUND

According to the classical theory, the role of activated platelets is to attach to collagen on subendothelial cells, or to each other, at the site of injury. Adhesion receptors on the surface of activated platelets cause the platelets to adhere to each other and aggregate at the site of the injury, resulting in the formation of a platelet plug that provides a physical barrier to stop blood flow out of the injured blood vessel. Activated platelets also release their intracellular granules that initiate vasoconstriction and an inflammatory response stimulating activation and activity in other cells. In addition to orchestrating the clotting processes that eventually stops the loss of blood, the contents of the platelets contain growth factors and other mediators that provides the environment needed to stimulate connective tissue to grow, migrate and heal the wound. Since a natural function of the intracellular contents of the platelets is to create an environment that stimulates cell growth, platelets typically used for transfusions can be fractured (lysed) through a series of freeze-thaw cycles to produce a lysate that is ideal as a tissue culture media. Unfortunately, the production of platelets from whole blood is limited by the time between collection and separation, typically within 8 hours. For example, 21 CFR 640.24 (b) specifies that whole blood or plasma can be held in storage between 20° C. and 24° C. before separation to obtain platelets, but that the separation must be within 4 hours of phlebotomy or within the time frame of the directions for use for the blood collecting, processing and storage system (generally 8 hours or less). Since platelet lysate can be produced from whole blood derived platelets, their production has conventionally been also limited to an 8 hour or less time frame.

There is a significant need to increase production of platelet lysate and enhance the production beyond current procedural limitations. This need is driven by the immergence of Cell and Gene Therapies that use platelet lysate as the growth media needed to produce these life saving drugs.

SUMMARY

The current disclosure is generally directed at methods of producing human platelet lysates (HPL) from platelets intended for transfusion purposes but have expired. More specifically, embodiments of the methods comprise producing whole blood derived platelets from a process not approved by the FDA for manufacturing platelets intended for transfusion in that the whole blood units have been placed at a refrigerated temperature below about 15° C., and optionally from about 0° C. to about 10° C., or from 2° C. to 8° C., or from about 2° C. to 6° C. prior to the separation of the platelets from the whole blood unit.

Typically, the whole blood undergoes centrifuging in a refrigerated centrifuge unit to thus separate components of the whole blood unit to produce platelet concentrate; and then conventional methods are used to make platelet lysate from these platelets manufactured from whole blood units refrigerated prior to separation.

In the method, the centrifuging can be carried out at a temperature below about 15° C., and optionally from 0° C. to 10° C., or from 2° C. to 8° C., or from about 2° C. to 6° C. Accordingly, throughout the process the platelets, whether part of the whole blood or separated into platelet concentrate, are maintained at the refrigeration temperature up to the production of platelet lysates.

The step of refrigerated centrifuging can comprise:

centrifuging the cold whole blood unit at a low RPM that create the g-force needed to separate components of the whole blood unit to produce platelet rich plasma; and centrifuging the platelet rich plasma at a high RPM, which is greater than the low RPM, to separate the platelet concentrate from the platelet rich plasma.

In embodiments of the method, the whole blood unit is refrigerated for more than 8 hours prior to performing the two centrifugation steps needed to produce a platelet concentrate. This method is outside 21 CFR 640.24 (b) and the directions for use for the blood collecting, processing and storage system making the platelet concentrate unsuitable for transfusion.

DETAILED DESCRIPTION

Figure 1:
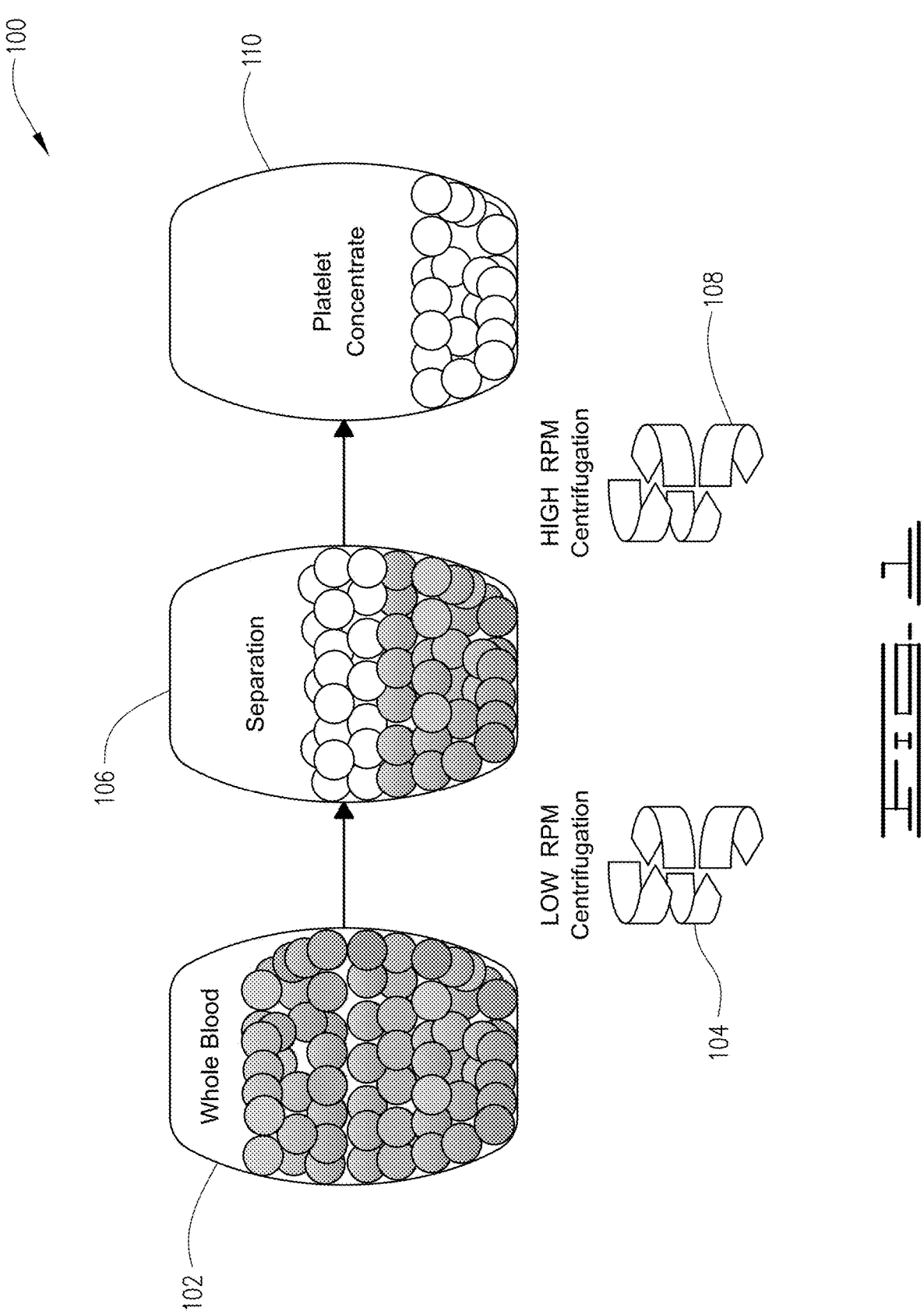
FIG. 1 is a schematic illustration of preparing platelet concentrate from whole blood in accordance with embodiments of this disclosure.

The present disclosure may be understood more readily by reference to these detailed descriptions. Numerous specific details are set forth in order to provide a thorough understanding of the various embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Before discussing the presently disclosed inventive concepts in detail by way of exemplary description and drawings, it is to be understood that the inventive concepts disclosed herein are not limited in application to the details of construction and the arrangement of the compositions, formulations, steps, or components set forth in the following description or illustrated in the drawings. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting except where indicated as such.

All of the compositions, devices, systems, and/or methods disclosed herein can be made and executed without undue experimentation in light of the present disclosure. Although certain steps are described herein and illustrated in the figures as occurring sequentially, some steps may occur simultaneously with each other or in an order that is not depicted.

As utilized in accordance with the present disclosure, the following terms, unless otherwise indicated, shall be understood to have the following meanings: the use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements, or method steps.

Throughout this disclosure, the terms "about", "approximate", and variations thereof, are used to indicate that a value includes the inherent variation or error for the device, system, the method being employed to determine the value, or the variation that exists among the study subjects.

The current disclosure is generally directed at methods of producing human platelet lysates (HPL) typically from expired platelet units that were initially manufactured to be infused into patients. Whole blood units from which platelets will be prepared for transfusion are maintained at a temperature cooling toward room temperature. Advantageously, the platelet lysate produced by the method can be formed from platelets that have been removed from the refrigerated whole blood units more than 8 hours after phlebotomy.

Broadly, the methods of this disclosure comprise the steps of providing a refrigerated whole blood unit; centrifuging the whole blood unit; and treating the resulting platelet concentrate to produce platelet lysates.

The first step of providing a refrigerated whole blood unit can comprise collecting one or more whole blood units into bags containing anticoagulant. Conventionally, whole blood units used for the preparation of platelets are cooled toward and maintained at a temperature near room temperature, such as from 16° C. to 24° C. or between 20° C. to 24° C. Further, the whole blood can only be held at this temperature for up to 4 to 8 hours after phlebotomy. After the prescribed period, the whole blood unit must be refrigerated and cannot be used to produce platelets for transfusion to patients.

In the current methods, the whole blood unit can be refrigerated at a temperature below about 15° C., and optionally from about 0° C. to about 10° C., or from 2° C. to 8° C., or from about 2° C. to 6° C. Further, the whole blood unit can be stored at the refrigerated temperature for periods of greater than 8 hours, greater than 12 hours, and even up to 48 hours after phlebotomy before being used to produce a platelet concentrate used to produce platelet lysate, as described below.

Once the whole blood unit(s) is obtained, it undergoes refrigerated centrifugal separation to separate it into component parts. The separation can be by one or more centrifugal separations and will typically be at the refrigeration temperature of below about 15° C., and optionally from about 0° C. to about 10° C., or from 2° C. to 8° C., or from about 2° C. to 6° C. For example, as illustrated in FIG. 1, the centrifugal separation is a two-step process 100.

In the first step 104, the cold whole blood unit 102 is centrifuged at a first speed (low RPM) to thus separate components of the whole blood unit to produce platelet rich plasma 106. This first centrifuged separation is at a low RPM so as to separate the red and white blood cells from platelets and plasma to produce platelet rich plasma but not so as to produce the platelet concentrated. The platelet rich plasma is then further centrifuged in second step 108, in which separation occurs at a higher RPM. Thus, in step 108, the cold platelet rich plasma is separated into its components to produce a cold platelet concentrate 110 enriched in platelets over the platelet rich plasma. The centrifugal separations can be carried out in any suitable refrigerated centrifuge and at any suitable RPM under the guidelines herein. The centrifuging can be carried out a temperature below about 15° C., and optionally from 0° C. to 10° C., or from 2° C. to 8° C., or from about 2° C. to 6° C. Accordingly, throughout the process the platelets, whether part of the whole blood or separated into platelet concentrate, are generally maintained at the refrigeration temperature up to the production of platelet lysates.

Figure 2:
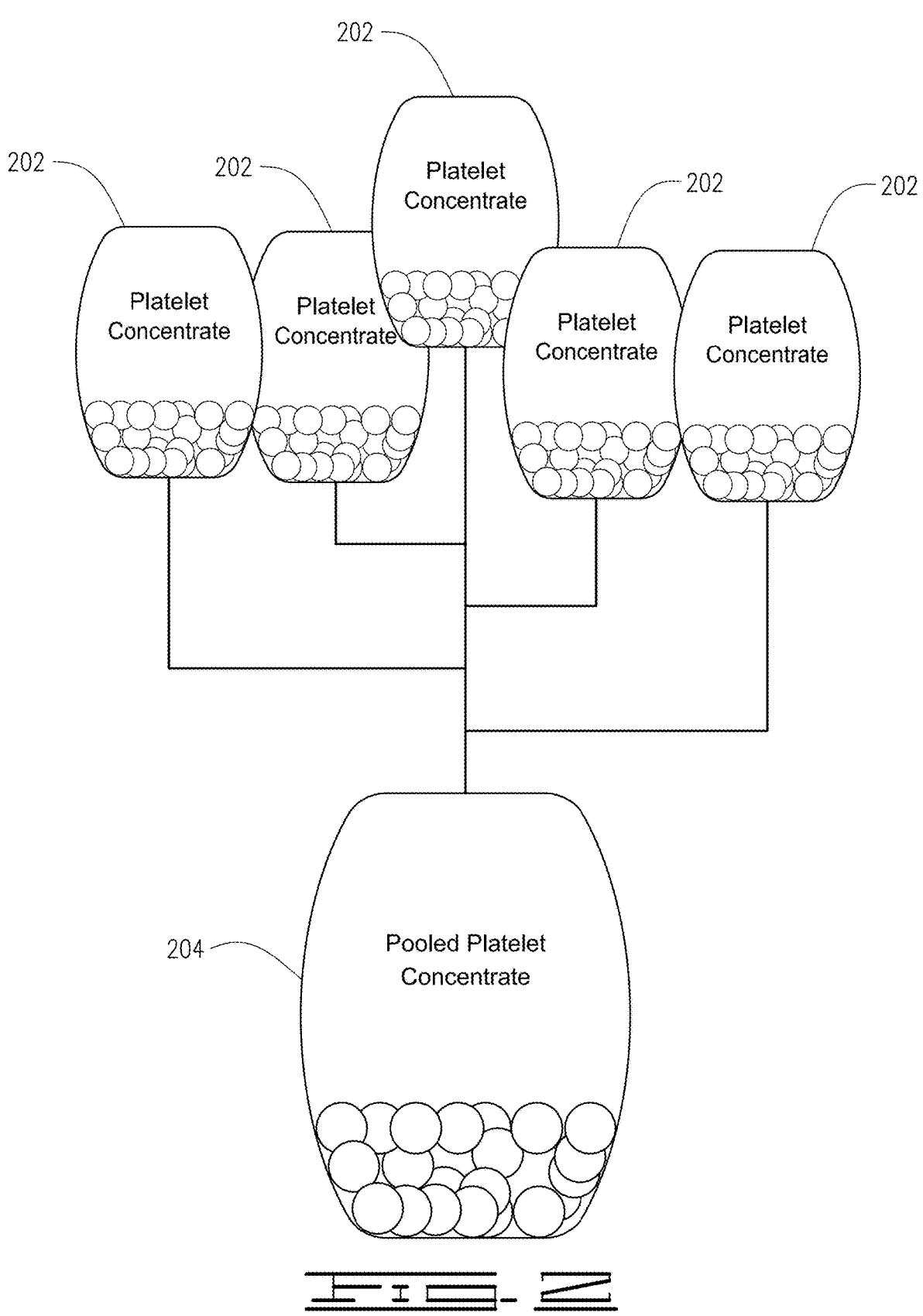
FIG. 2 is a schematic illustration of pooling platelet concentrate for the preparation of human platelet lysate.

The platelet concentrate prepared from refrigerated whole blood units can be used to produce platelet lysate. In embodiments, platelet concentrate 202 from two or more refrigerated whole blood units are pooled 204 and used as raw material to prepare HPL, as illustrated in FIG. 2. The platelet lysate can be prepared from the platelet concentrated by methods known in the art, such as by cycling through freezing and thawing so as to lysate the platelets.

Human platelet lysate (HPL) prepared by the above method from refrigerated whole blood up to 48 hours after phlebotomy are equivalent to HPL made from room temperature units in the prescribed time of less than 8 hours. The HPL prepared from platelets manufactured from refrigerated units in accordance with this disclosure can be used for the same purposes as conventionally prepared HPL. For example, they can be used as a supplement in tissue cultures, and they can be used to promote tissue growth when applied directly or indirectly into or upon damaged human tissue.

Other embodiments of the present invention will be apparent to one skilled in the art. As such, the foregoing description merely enables and describes the general uses and methods of the present invention. Accordingly, the following claims define the true scope of the present invention.

What is claimed is:

1. A method of producing a human platelet lysate (HPL) from platelets, the method comprising:
    providing a refrigerated whole blood unit which has a refrigerated temperature of 1° C. to 6° C., wherein the refrigerated whole blood unit comprises platelets;
    producing a platelet concentrate from the platelets in the refrigerated whole blood unit; and
    treating the platelet concentrate to produce the human platelet lysate.

2. The method of claim 1, wherein the refrigerated temperature is from 2° C. to 6° C.

3. The method of claim 1, wherein the refrigerated temperature is from 2° C. to 4° C.

4. The method of claim 1, wherein the step of providing the refrigerated whole blood unit comprises:

collecting one or more whole blood units into bags containing anticoagulant;

cooling the whole blood unit to a near-room temperature of 16° C. to 24° C.;

maintaining the whole blood unit at the near-room temperature for no more than 8 hours; and after the step of maintaining, cooling the whole blood unit to the refrigerated temperature to produce the refrigerated whole blood unit.

5. The method of claim 4, wherein the whole blood unit is stored at the refrigerated temperature for a period of 8 hours to 48 hours between the step of cooling to the refrigerated temperature and the step of producing the platelet concentrate.

6. The method of claim 5, wherein the platelets, whether part of the whole blood or separated into the platelet concentrate, are maintained at the refrigerated temperature from the step of cooling to the refrigerated temperature to the step of producing the human platelet lysate.

7. The method of claim 1, wherein the refrigerated whole blood unit is expired such that the refrigerated whole blood unit is not suitable for transfusion purposes under applicable guidelines.

8. The method of claim 1, wherein the step of producing the platelet concentrate maintains the refrigerated temperature.

* * * * *